United States Patent
Hamunen et al.

(10) Patent No.: US 7,371,876 B2
(45) Date of Patent: May 13, 2008

(54) PROCESS FOR THE PURIFICATION OF STEROLS FROM HYDROCARBON EXTRACTS USING EVAPORATIVE FRACTIONATION

(75) Inventors: Antti Hamunen, Raisio (FI); Keijo Ukkonen, Kuusankoski (FI)

(73) Assignee: Sterol Technologies Ltd., Raisio (FI)

( * ) Notice: Subject to any disclaimer, the term of this patent is extended or adjusted under 35 U.S.C. 154(b) by 77 days.

(21) Appl. No.: 10/931,043

(22) Filed: Sep. 1, 2004

(65) Prior Publication Data
US 2005/0033068 A1 Feb. 10, 2005

Related U.S. Application Data

(63) Continuation of application No. 09/926,397, filed on Dec. 10, 2001, now abandoned.

(51) Int. Cl.
*C07J 9/00* (2006.01)
(52) U.S. Cl. ...................................... 552/545
(58) Field of Classification Search ................ 552/545
See application file for complete search history.

(56) References Cited

U.S. PATENT DOCUMENTS

| 2,530,810 A | 11/1950 | Christensen et al. |
| 3,691,211 A | 9/1972 | Donald |
| 3,887,537 A | 6/1975 | Harada et al. |
| 4,076,700 A | 2/1978 | Harada et al. |
| 2,866,797 A | 5/1979 | Manly et al. |
| 4,153,622 A | 5/1979 | Lamminkari et al. |
| 4,254,024 A | 3/1981 | Stewart et al. |
| 6,297,353 B1 | 10/2001 | Diaz et al. |
| 6,462,210 B1 | 10/2002 | Diaz et al. |

FOREIGN PATENT DOCUMENTS

| WO | WO 99 16785 | 4/1999 |
| WO | WO 99 42471 | 8/1999 |

*Primary Examiner*—Barbara P. Badio
(74) *Attorney, Agent, or Firm*—Arent Fox LLP

(57) ABSTRACT

The present invention describes a method for separating sterols from neutral substances comprising the sterols. The method generally starts with extracting a hydrocarbon fraction from neutral substances. The hydrocarbon fraction may be optionally washed with water. The neutral substances are separated from the hydrocarbon. The hydrocarbon fraction or the neutral substances are subjected to evaporation fractionating to obtain a sterol-rich fraction. The sterol-rich fraction is dissolved in a solvent, and the sterols are crystallized from the solvent. The obtained sterol crystals are separated from the solvent.

21 Claims, No Drawings

PROCESS FOR THE PURIFICATION OF STEROLS FROM HYDROCARBON EXTRACTS USING EVAPORATIVE FRACTIONATION

This application is a continuation of U.S. application Ser. No. 09/926,397, filed Dec. 10, 2001, now abandoned, which claims priority under 35 USC § 119(e) of U.S. Provisional Application Ser. No. 60/131,303, which is hereby incorporated by reference.

FIELD OF THE INVENTION

The present invention relates to a purification method, and more particularly to an improved method for separation of commercially important sterols from neutral substances or refined neutral substances, which have been separated from soaps.

BACKGROUND OF THE INVENTION

Sterols useable in pharmaceuticals and foods need to be purified to quite a high degree to exclude undesired components, such as inorganic salts and soap residues existing in the neutral substances. Although usually present in low concentrations, a part of these impurities usually tend to remain in the sterol fraction, if the isolation of sterols has been performed by known straight crystallization processes without any particular purification steps. The neutral substances in most cases also contain organic impurities, which usually makes direct crystallization of sterols in pure form difficult. One kind of impurity is a group of compounds which typically cannot be seen in gas chromatographic analyses usually used in sterol assays. The exact nature of these compounds is not known, but there is some evidence that this group consists of a wide molecular weight range hydrocarbon-type material. Because of its invisibility in gas chromatographic analysis, the material is often called "nonelutable compounds" or "nonelutables". Also the lighter components of the neutral substances may sometimes interfere with the crystallization of sterols. In a typical case, when the neutral substances are originated from wood pulping, this light fraction typically consists of impurities such as di- and sesquiterpene compounds, stilbenes and wax alcohols.

Sterols have previously been crystallized from sterol containing materials, typically from neutral substances, using alcohol, ketone or hydrocarbon solvents, without or with water (U.S. Pat. Nos. 2,704,764, 2,729,655, 2,843,610, 5,117,016, 4,420,427). None of these methods work quite satisfactorily in the most usual cases where the substance that contains sterols also contains the impurities noted above.

U.S. Pat. No. 2,870,176 discloses a method of obtaining stigmasterol from a phytosterol solution in which a phytosterol sample is dissolved in hexane and a stigmasterol-enhanced fraction is crystallized from the cooled solution. After separation from the hexane solvent, the stigmasterol-enhanced fraction is redissolved in hexane and recrystallized several times, to obtain substantially pure stigmasterol crystals. There is no disclosure of a step whereby any impurities are separated from the phytosterol fraction.

U.S. Pat. No. 3,965,085 discloses a method for extracting neutral substances from soaps in which a hydrocarbon solvent is used to extract the neutral substances, and thereafter the neutral substance solution phase is evaporated whereby a residue is obtained containing mainly sterols, terpene alcohols, hydrocarbons and other unsaponifiable substances. This solution is cooled to obtain crystalline material. The crystalline material contains sterols, along with fatty alcohols and terpene alcohols. There is no disclosure of a purification method for purifying the sterol crystals. In addition the method does not include any evaporation fractionation step.

U.S. Pat. No. 4,076,700 discloses a process for recovering fatty acids and/or rosin acids and optionally sterols from a tall oil skimming soap or a tall oil soap. According to one embodiment of this process, the soap is first saponified with an alkali to decompose esters of rosin acid and fatty acid with sterols and other alcohols, and the thus obtained saponification product is subsequently introduced into a thin film evaporator to evaporate and remove water and low boiling unsaponifiables. The product of this stage can again be introduced into the thin film evaporator to evaporate and separate sterols and heavy unsaponifiables. For the production of pure sterols, this proposed process is very complicated. In addition, this proposed process does not use the technique of extracting neutral substances from soaps.

SUMMARY OF THE INVENTION

It has now been realized that in order to remove the impurities interfering with sterol crystallization from the extracted neutral substance, it may be necessary to apply various processes/process combinations, depending on the type of impurity to be removed. The unit operations in question connected with this invention include evaporation fractionation of the impurities in the neutral substance, and optionally high temperature water wash of the neutral substances, before the evaporation fractionation.

This invention relates to a method for producing in good yields high quality, high purity sterols, the method comprising extraction of neutral substances from soaps, removal of components interfering with sterol separation from the neutrals (e.g., impurities), and sterol crystallization from the purified neutral substances.

In one aspect of the present invention there is provided a method for the separation of sterols from soaps comprising preparing a hydrocarbon fraction rich in neutral substances from a soap, optionally washing the hydrocarbon fraction with water, optionally separating the hydrocarbon and the neutral substances, evaporation fractionating the hydrocarbon fraction from step (a) or (b) or the neutral substances from step (c) to obtain a sterol-rich fraction, dissolving the sterol rich fraction in a solvent system and crystallizing the sterols from the solvent system, and separating the obtained sterol crystals from the solvent.

The separated sterol product obtained by the method according to the present invention contains practically only sterol components derived from the neutral substance, without any interfering salt or organic impurities, which would make crystallization purification difficult. A further advantage of the method according to this invention is that, in addition to the high purity, simultaneously very high sterol yields are obtained.

DESCRIPTION OF THE PREFERRED EMBODIMENTS

The neutral substances (unsaponifiables or neutrals) can be obtained by extracting from soaps. Any soap of vegetable origin may be used. Neutral substances suitable as raw material in the method according to the present invention may therefore be obtained from extracts of vegetable origin such as soaps from vegetable oils, or preferably from crude soap from the sulfate cellulose process or pitch soap obtained from tall oil. The method according to the present invention is preferably suitable for neutral substances obtained from soap originated from wood pulping.

The neutral substances can be obtained from soaps typically by extraction. Extraction of these neutral substances from soaps can be performed, for example, by using hydrocarbon solvents at elevated temperatures and pressures, or using mixtures of hydrocarbons and ketones and/or lower alcohols as extraction solvents (for example, as shown in U.S. Pat. No. 3,965,085, hereby incorporated by reference).

Preferably the hydrocarbon fraction which is rich in neutral substances is prepared by extracting the soap with a hydrocarbon solvent followed by the separation of the hydrocarbon phase from the soap phase. If only hydrocarbon is used as a solvent, the extraction may preferably be performed at elevated temperatures (optionally at elevated pressures, as well) in order to break the emulsion which may otherwise be formed.

Preferably the hydrocarbon extraction of the soap is a high temperature extraction wherein the temperature preferably is at least 140° C., and more preferably between 140° C. and 190° C. If the extraction is conducted in a closed system, as preferred, the pressure in the system is at least equal to the vapor pressure of the extraction mixture at the temperature used for extraction.

Typical extraction conditions are, for example: the hydrocarbon used as extraction solvent is heptane, the solids content in the soap to be extracted is about 25-40%; the amount of the solvent used in the extraction is more than one part per one part of dry soap by weight; the extraction temperature is higher than 140° C.; and the pressure is more than 10 bars. The extraction can be performed by using any known extraction method (batch extraction, column, mixer-settler, etc.).

In the extraction, the weight ratio of soap in dry weight:water of the extraction mixture:hydrocarbon solvent of the extraction mixture can be 1:>1:>1, preferably 1:1-3:2-6, more preferably 1:2-3:3-6, and most preferably 1:2-3:4-5.

Preferably the washing step (b) is a high temperature water wash conducted in a closed system, wherein the temperature preferably is between 120° C. and 190° C. and the pressure is preferably the pressure prevailing at that temperature. Preferably the water wash is done directly after the high temperature hydrocarbon extraction of the soap (if this technique is applied for producing the neutral substance). Approximately the same temperature and pressure conditions can be applied in the extraction step and the washing step.

By the high temperature water wash, traces of inorganic salts and soap residues can be removed. These impurities typically exist only in low concentrations, but give the sterol product an ugly gray or brownish color, if the product is crystallized without removing them. The soaps present in the neutrals usually also make filtration of the crystallized sterols difficult. The high temperature water wash of neutrals has preferably to be performed in a closed system at high temperature (e.g., about 140° C. or higher) and high pressure (e.g., above the prevailing pressure at the water temperature), if there is any tendency of emulsion formation during the wash. The amounts of water to neutral substance (hydrocarbon) phase may vary in a broad range; e.g. weight ratios from 1:10 to 10:1 can be applied depending on the amount of impurities included. It has been shown that the water wash removes only undesired impurity components, and practically does not affect the sterol content of neutral substances.

Neutral substances can be separated from the hydrocarbon phase by evaporating the same to dryness, filtration or centrifuging, as well known in the art.

Evaporation fractionation of impurities can be applied in connection with the water wash, or it can be used instead of it. By using short path distillation (e.g. thin film or wiped film) the components lighter than sterols can be removed, leaving the sterol-rich fraction as the bottom fraction. The typical applicable conditions are, for example, 0.1 mbar pressure and 160° C. temperature. The time is not critical, and can be as little as several seconds, as the evaporation step is normally continuous. The evaporation removes, for example, diterpene compounds, stilbenes and wax alcohols interfering the subsequent crystallization of sterols. The removal of these components can further be improved by using a rectification column in connection with the short path evaporation.

The content of these impurities in typical neutral substances originated e.g. from wood pulping, may be up to 30-40%. The sterols can be crystallized from the evaporation bottoms. The advantage is that because of increased sterol content in the thus refined neutral substance and removal of interfering components, the yield and the purity of the sterol product will be better than without evaporation fractionation. However, this type of evaporation in most cases does not remove all of the inorganic salts and soap residues. Thus, to obtain still better results, it is advantageous to combine the evaporation fractionating step with the high temperature (and preferably, high pressure) water wash pretreatment.

The evaporation fractionation of the neutral substance can also be implemented so that the sterol-rich fraction is evaporated and accordingly separated from the heaviest components of the neutral substance. In this case, inorganic salts and soap residues will also be separated from the sterol fraction. Thus, no separate water wash procedure is needed in this case. Evaporation of the light fraction can be a preceding part of the evaporation of the sterol fraction in order to most efficiently fractionate the interfering impurity components. Typical conditions for evaporation of the sterol rich fraction are e.g. pressure 0.1 mbar, temperature 220° C., time as indicated above. It has been shown that the sterols contained in the evaporation feed can be recovered practically quantitatively to the distillate when having proper distillation conditions. Thus, no significant sterol losses will take place during this purification step. Taking into account that the sterol content in the sterol-rich fraction during evaporation fractionation can be increased typically from 25-30% content in the original neutral substance to over 40-60% in the fractionated sterol-rich distillate fraction, and this taking place without any substantial sterol losses, it is clear that this purification offers a very good starting point for the crystallization purification step of sterols.

Crystallization of the sterols from the sterol-rich fraction can be performed by using any known solvent or solvent combination. However, particularly advantageous is to use hydrocarbons combined with water, or even more preferably may be the use of combinations of hydrocarbons, water and a lower ($C_1$-$C_6$) alkanol, especially methanol.

Preferably the hydrocarbon solvent used in this invention is a short chain, aliphatic or cycloaliphatic hydrocarbon containing 1-10 carbon atoms, preferably 5-8 carbon atoms. Preferred hydrocarbon solvents are hexane, heptane, octane, cyclohexane, methylcyclohexane and mixtures thereof.

In the crystallization solvent system the weight ratio of hydrocarbon:lower alkanol:water is preferably 1.5-5:0-0.5: 0-1, and more preferably 1.5-3.5:0.03-0.035:0-1.

In the crystallization step, the weight ratio of the sterol-rich fraction in dry weight:solvent system is preferably 1:1.5-6.5, and more preferably 1:1.5-5.

After the crystallization step, the sterol crystals are preferably washed with any suitable solvent or solvent system, preferably with a solvent system which is the same as the crystallization solvent system.

The following examples illustrate the invention in more detail. The %-figures mean % by weight. The term purity means the content of identified sterol components. The sterol product contains also small amounts of probably closely related, but not exactly identified, sterol-like components, which behave like the sterols in question and cannot be removed using these processes. Thus, the maximum purity practically attainable by these purification processes is about 98%.

EXAMPLE 1

The unsaponifiables (from *Pinus taeda* based pitch soap) used in this crystallization were in a hydrocarbon solvent (a mixture of aliphatic and cycloaliphatic hydrocarbons, LIAV110 delivered by Neste Oy). The mixture of solvent and unsaponifiables was brought directly from the soap extraction, which was performed at 170° C. and 18 bar pressure in a pressure autoclave. The material ratios of the components were 1 part dry soap, 2 parts water and 4 parts solvent. After 5 minutes at extraction temperature mixing was stopped and the layers were allowed to separate. The lower water phase was separated through a cooled sampling bomb when the contents were still hot. Solids content in the remaining hydrocarbon phase was 11.3%, and the sterol content was 35% of the solids. The hydrocarbon phase was allowed to cool slowly to 20° C. The precipitated sterols were filtered and washed with fresh solvent. From 100 g of dry neutrals 22.5 g of a sterol blend was obtained, consisting of sitosterol, sitostanol, campesterol and campestanol and nonelutable impurities. The color of the product was light grey/brown. The ash content describing the amount of inorganic salts was 0.4%. The sterol content was 80%.

EXAMPLE 2

10 l of the hydrocarbon phase of example 1 was put into an autoclave and 5 l water was added. The autoclave was closed and the temperature was raised to 130° C. simultaneously stirring the contents. After 5 minutes at 130° C. the stirring was stopped and the lower water phase was separated through a water cooled sampling bomb. The hydrocarbon phase was let to cool to 20° C. The crystallized material was filtered and washed with fresh hydrocarbon. The color of the resulting crystalline crude sterol was white and the ash content was 0.09%. The purity of the sterols was 82% and the yield 23 g/100 g feed neutral substance.

EXAMPLE 3

This example is a reference example for crystallization of sterols from unsaponifiables using a hydrocarbon/methanol/water mixture as crystallization solvent without any other refining processes.

A sample of dried *Pinus radiata* unsaponifiables, which were produced by hexane-acetone extraction (e.g. according to U.S. Pat. No. 3,965,085), were dissolved into a LIAV110/methanol/water solvent mixture in ratios 1/3/0.3/0.1 (by weight) by heating to boiling temperature. Sterols were crystallized by cooling the temperature slowly to 25° C., and separated by filtration using a Buchner funnel. Washing was accomplished with a pure crystallization solvent mixture in small portions, the amount and content of it being the same as in the crystallization step. The yield of dried product was 73%, purity 93% and ash content 0.35%.

EXAMPLE 4

*Pinus radiata* unsaponifiables extracted using a commercial hexane-acetone extraction (solvent content 5%) were dried from residual solvents using short path evaporation (the equipment was the wiped film evaporator KDL-5, manufactured by UIC). The conditions were: pressure 10 mbar and evaporator temperature 150° C. in the jacket of the equipment. The solvent free neutrals were led to the wiped film evaporator to remove the light neutrals fraction. The conditions in this unit were: pressure 0.1 mbar and temperature 160° C. The distillate (30% of the feed), which contains light neutrals, contained 3% of the original sterol content of the feed. A sample of the bottom fraction from this distillation (sterol content about 46%) was dissolved by refluxing in LIAV110/methanol/water (3:0.3:0.1, 1 part of the bottom fraction (dry weight)/3.4 parts of solvent) and the sterol fraction was crystallized by cooling the mixture slowly to 25° C. After similar separation procedures as in example 3, the sterol yield recovered was 79% of the sterol content in the original neutral substance and the sterol purity was 96.5%. The ash content in the sterol product was 0.37%.

EXAMPLE 5

The rest of the bottom fraction from the distillation performed in Example 4 was fed again to the wiped film evaporator. Now the evaporation conditions were: pressure 0.1 mbar, temperature 225° C. 95% sterols of the feed were recovered to the distillate, where the sterol concentration was 51%. A sample of the distillate was dissolved in a LIAV110:MeOH:water blend in the same ratios as in Example 4 (1:3:0.3:0.1). After crystallization, filtration separation and washing with a solvent similar to the crystallization solvent, the yield of dried sterol was 83% of the sterol content in the distillate and the purity was 97.5%. The color of the product was very white and ash content was only 0.01%.

EXAMPLE 6

Another sample of the distillate prepared in Example 5 was dissolved in a LIAV110/water mixture in ratios distillate:LIAV:water 1:7:1. The crystallization procedure was as in the previous examples. The yield of dried sterols was 77% and the purity was 97.5%.

EXAMPLE 7

The neutral substance was prepared and washed as in example 2. The solvents were removed by using a rotavapor. The light fraction was removed from the dried neutrals by evaporating with a KDL-5 wiped film evaporator (0.1 mbar, 163° C. temperature in the jacket). The yield of the light fraction was 32%, and the total sterol loss to the light fraction was 4%. A sample of the distillation residue was dissolved, crystallized and separated from a LIAV/methanol/water solvent and washed as in example 4. The sterol yield was 80% and the purity was 97.5%. Ash content of the almost white product was 0.1%.

EXAMPLE 8

The feed material was *Pinus radiata* wood based unsaponifiables extracted by hexane-acetone solvent extraction. The dried unsaponifiables were fed to a wiped film evaporator equipped with a rectification column. The temperature of the feed neutrals was 150° C., the temperature in the bottom part of the column was 207° C., in the top part of the column 189° C., and in the residue 241° C. (the jacket temperature was 298° C.). The pressure inside the equipment was 2.2 mmHg. The amount of light fraction distilled over was 23% and the amount of residue was 76%. The sterol loss into the light fraction was only 0.4%. Sterol content in the residue was 48.1%.

The residue from this distillation was fed into a short path distillation equipment. The conditions there were: pressure 0.1 mmHg, feed temperature 149° C., jacket temperature 312° C., condenser temperature 112° C., temperature of residue 184° C. The sterol yield of the distillate in this evaporation was 95% of the feed mass (residue 5% of the feed). The sterol concentration in the distillate was 51.5%, and in the residue 9%. The loss of sterols in this distillation was only 1%.

A sample of the distillate was dissolved in a LIAV110/methanol/water solvent and sterols were crystallized, separated and washed with a solvent similar to the one used in the crystallization, as in previous examples. The sterol yield was 83% and the purity was 97.8%. Ash content of the product was 0.01%.

What is claimed is:

1. In a process for separating sterols from neutral substances including evaporation fractionation to remove a light fraction of the neutral substances, the improvement comprising performing the evaporation fractionation utilizing an apparatus comprising a wiped film evaporator equipped with a rectification column and a short path distillation equipment.

2. A process for separating sterols from neutral substances comprising
   extracting the neutral substances from soaps and drying the neutral substances;
   feeding the dried neutral substances into a wiped film evaporator equipped with a rectification column;
   performing evaporation fractionation to remove the light fraction of the neutral substances and to obtain a residue;
   feeding the residue into a short path distillation equipment, and distilling a sterol-rich fraction; and
   dissolving the sterol-rich fraction in a solvent, and crystallizing and separating the sterols.

3. The process of claim 2, wherein the extraction is accomplished by extracting a soap with a mixture of a hydrocarbon and a ketone and/or a lower alcohol as extraction solvents.

4. The process of claim 2, wherein the extraction is accomplished by extracting a soap with a hydrocarbon solvent, and thereafter separating the hydrocarbon phase from the soap phase.

5. The process of claim 4, wherein the extraction is carried out at a temperature of at least 140° C.

6. The process of claim 5, wherein the temperature is between 140° C. and 190° C.

7. The process of claim 4, wherein said extracting step is conducted with an extraction mixture comprising the soap, water and the hydrocarbon solvent, which are present in the extraction mixture at a weight ratio of 1:>1:>1.

8. The process of claim 7, wherein the soap, water and the hydrocarbon solvent are present in the extraction mixture at a weight ratio of 1:>1-3: 2-6.

9. The process of claim 7, wherein the soap, water and the hydrocarbon solvent are present in the extraction mixture at a weight ratio of 1:2-3:3-6.

10. The process of claim 7, wherein the soap, water and the hydrocarbon solvent are present in the extraction mixture at a weight ratio of 1:2-3:4-5.

11. The process of claim 3, wherein the hydrocarbon in the hydrocarbon fraction is selected from the group consisting of hexane, heptane, octane, cyclohexane, methylcyclohexane and mixtures thereof.

12. The process of claim 4, wherein the hydrocarbon in the hydrocarbon fraction is selected from the group consisting of hexane, heptane, octane, cyclohexane, methylcyclohexane and mixtures thereof.

13. The process of claim 2, wherein the solvent comprises a hydrocarbon and water.

14. The process of claim 2, wherein the solvent comprises a mixture of a hydrocarbon, a $C_1$-$C_6$ alkanol and water.

15. The process of claim 14, wherein the $C_1$-$C_6$ alkanol is methanol.

16. The process of claim 14, wherein the solvent is a mixture of the hydrocarbon, the $C_1$-$C_6$ alkanol and the water, in a weight ratio of 1.5-5:0-0.5:0-1.

17. The process of claim 16, wherein the weight ratio is 1.5-3.5:0.03-0.35:0-1.

18. The process of claim 2, wherein the sterol-rich fraction and the solvent are present in a weight ratio of 1:1.5-6.5, based on the dry weight of the sterol-rich fraction.

19. The process of claim 18, wherein the weight ratio is 1:1.5-5.

20. The process of claim 2, comprising the further step of washing the sterol crystals after the crystallizing step.

21. The process of claim 20, wherein the crystals are washed with a solvent which is the same as the solvent used in the crystallization.

* * * * *